United States Patent [19]
O'Neill et al.

[11] 3,988,585
[45] Oct. 26, 1976

[54] THREE-DIMENSIONAL RECTILINEAR SCANNER

[75] Inventors: William J. O'Neill, Ann Arbor; Donald R. Strange, Howell; Philip A. Miller, Ann Arbor, all of Mich.

[73] Assignee: Medical Data Systems Corporation, Ann Arbor, Mich.

[22] Filed: June 5, 1975

[21] Appl. No.: 583,917

Related U.S. Application Data

[63] Continuation-in-part of Ser. No. 478,233, June 11, 1974, abandoned.

[52] U.S. Cl.............................. 250/363 S; 250/367; 250/505
[51] Int. Cl.² ........................................ G01T 1/20
[58] Field of Search ................. 250/367, 505, 363 S

[56] References Cited
UNITED STATES PATENTS

| | | | |
|---|---|---|---|
| 2,942,109 | 6/1960 | Bell et al............................. | 250/367 |
| 3,197,638 | 7/1965 | Sinclair............................... | 250/274 |
| 3,509,341 | 4/1970 | Hindel et al. ....................... | 250/321 |
| 3,777,148 | 12/1973 | Miraldi .............................. | 250/505 |

Primary Examiner—Harold A. Dixon
Attorney, Agent, or Firm—Albert H. Graddis; Jeremiah J. Duggan

[57] ABSTRACT

A rectilinear scanner for detecting radiation in a plurality of channels utilizing a collimator. Each of the channels receives information from a different portion of the collimator. Information separately received is separately massaged and later collated to present a common image. The information is processed by apparatus in a data processing system. This system has means for massaging analog signals corresponding to gamma radiation counts. This system has means for converting such analog signals to digital signals. This system has means interfacing the digital signals into an address register that communicates directly via data busses to core memory of a central processing unit by cycle stealing. This system has means deriving clinically significant information by computation on the resultant digital data. This system has means storing, retrieving, and displaying the resultant digital data and the resultant derivations therefrom collectively. This is done in such a manner as to allow time sequencing of the aforementioned operations such that the aforementioned operations can be interleaved on a real time basis.

13 Claims, 44 Drawing Figures

| FIG. | Δ Cent. | SOURCE |
|---|---|---|
| 12,13 | 3 | 20 |
| 2,3 | 14 | 70 |
| 17,18 | 20 | 90 |

| Fig. | ΔCent. | Source |
|------|--------|--------|
| 20,21 | Q | R |
| 8,9 | ~Q | ~R |

THREE-DIMENSIONAL RECTILINEAR SCANNER

This application is a continuation-in-part application of U.S. Pat. application Ser. No. 478,233, filed June 11, 1974, now abandoned.

This invention relates generally to a gamma ray image scanner. More particularly, this invention relates to a gamma ray imaging device utilizing a rectilinear scanner and providing stereoscopic images.

A gamma ray image scanner includes a camera-like device, often called a "head," for detecting gamma ray radiation. The source of such radiation is a radioactive material induced into or transmitted through the body of a patient. For example, within the body, depending upon the carrier or chemical medium in which the radioactive substance is carried, the radioactive substance will concentrate in certain portions of the patient's body. By detecting these radiation concentrations, a picture of the patient is obtained with the radiation concentration highlighted. Such a picture may be displayed on a cathode ray oscilloscope.

Such gamma ray imaging devices in the past have included a cathode ray oscilloscope for display purposes as well as a camera or head for detecting gamma ray radiation. In addition, these devices have utilized data processing equipment including a general purpose computer as well as an analog to digital converter used to convert electrical signals corresponding to the radiation concentrations detected by the camera or head. This involves converting these signals to digital pulse signals that can be processed by the general purpose digital computer.

Gamma ray imaging devices as used in the past have also utilized devices for funneling the radiation detected along a predetermined path. Commonly a collimator has been used for this purpose. A collimator is basically a piece of lead with apertures or channels in it. The radiation passes through the channels but not through the lead. Thus radiation can be detected from a particular location by funneling that radiation through the collimator and, in effect, putting blinders on the head or camera, preventing the head or camera from looking at radiation other than that detected along the funneled path.

Generally, imaging devices in the past have been utilized by passing the camera or head along a predetermined rectilinear path, that is criss-crossing the patient in a predetermined path. A picture of the gamma radiation in the patient is obtained on the basis of information collected during this rectilinear scan.

One of the problems of such devices in the past has been an inability to pick up significant medical information. Such information corresponds to particular concentrations of radiation within the body of the patient remote from the focal plane of the scanner. This is due to the rectilinear scan being confined to a focal plane for a two-dimensional picture for a predetermined scan. Previous attempts to cure this problem in obtaining a third dimension have met with frustration. This is in part due to time differentials for different scans along different predetermined paths corresponding to different planes within the body of the patient.

The present invention relates to a gamma ray imaging device utilizing a rectilinear scanner in providing stereoscopic images. The present invention differs in structure from prior devices using rectilinear gamma ray imaging. Instead of having a single crystal generating electrical signals corresponding to radiation passing through the funnels of the collimator, or instead of having a plurality of crystals simultaneously generating electrical signals corresponding to the radiation passing through all the funnels in a collimator, two crystals, or two separate arrays of crystals, are utilized to generate electrical signals discretely from different funnels of the same collimator. For example, in its preferred embodiment, the present invention has one crystal or one plurality of crystals responsive to radiation passing through the funnels in the collimator on the left side of the collimator, while another crystal or another plurality of crystals, generates signals responsive to radiation passing through the funnels in the collimator on the right side of the collimator. The collimator used in the preferred embodiment of this invention has all of the funnels or passages with axes directed toward a common focal plane.

Thus, in the preferred embodiment of the subject invention, two different channels of information are simultaneously obtained. Information from one channel being from the right side only of the collimator. Information from the other channel being from the left side of the collimator. Neither of the two channels of information derive radiation detected from a common funnel or passage of the collimator. In other terms, this means that radiation passing through the funnels or passages within the collimator on the right side of the collimator are separated and discretely detected, while simultaneously, information corresponding to radiation passing through the funnels or passages on the left side of the collimator are separately and discretely detected.

These two separate channels of information are then processed independently and discretely by the analog to digital converter, and also separately and discretely by the general purpose computer.

In the preferred embodiment of the present invention, the information obtained from the two separate channels can be projected simultaneously on a cathode ray oscilloscope. Because the two streams of information are derived from intersecting focal axes of the collimator, a three-dimensional effect can be observed. Thus, a so-called thin shell of concentration of radiation spaced at a distance from the intersection of focal planes, will appear as significant information on a stereoscopic display.

In the preferred embodiment of the subject invention, the separate channels of information can be massaged by the general purpose computer in order to obtain difference calculations. The term "difference calculations" as used herein, refers to the different responses from the same concentration of radiation obtained by the two channels of information. These calculations can be approximated by programmed data handling in the general purpose digital computer which is a part of the embodiment of this invention in this alternative.

Exemplary understanding of the operation of the immediately aforementioned alternative embodiment of this invention can be gleaned by utilizing a test run of the device. This is a test for determining data for such difference computations generated by passing the rectilinear scanning camera or head over predetermined sources of radiation. These sources have predetermined strength and are spaced at predetermined distances from one another in three dimensions. The difference in radiation response eminating from these predetermined source strengths at predetermined distances can then be stored in the computer. Subsequently, a table can be derived by computer from this data that will form a matrix in which the different radiation responses will be correlated with the predetermined distances and radiation source strengths.

In this manner, upon subsequent rectilinear scans over sources of radiation in which the strength of radiation and the location of radiation sources with respect to each other are not predetermined, the radiation strength obtained as data by the two separate channels can then be compared to the previously generated matrix in order to determine or at least approximate the differences in depth from such sources of radiation. This enables a presentation of a mathematical graph, chart, or other representation of the resultant table-look-up operation to determine the difference calculations and to present same. The representation can be done on a cathode ray oscilloscope by numbers, charts, or graphs. Alternatively, a massaging of the data for presentation on the cathode ray oscilloscope can be obtained so the radiation picture can be corrected on the basis of data obtained through the camera compared with the data stored in the matrix.

Accordingly, it is an object of the present invention to obtain a simultaneous discrete scan using separate channels with different focal planes. In this manner, problems with subsequent or time differentiated scans resulting in obscuring of medically significant information or in highlighting of noise or medically insignificant information can be sharply reduced if not eliminated.

It is another object of this invention to provide simultaneous multi-channel rectilinear scans for obtaining difference calculations for determining depth or displacement from focal planes of radiation in a manner that is relatively inexpensive and yet capable of being used in conjunction with analog to digital conversion apparatus as well as a general purpose computer for computations and display and massage of data.

It is still another object of this invention to provide a gamma ray imaging device with separate channels that separately, distinctly, and discretely detect radiation in a manner that reduces the obscuring of data otherwise clumped on a single common focal plane.

It is still another object of this invention to provide separate discrete channels of obtaining and massaging data corresponding to radiation concentrations utilizing a collimator that has a common focal plane for all of the channels used separately and discretely in order to obtain data corresponding to differences of radiation distribution in three-dimensional space.

One of the purposes of this invention is to provide a "datum level" for giving a uniform response prior to data acquisition. The raw data is in the form of signals from photomultiplier tubes. These signals correspond to distance from source and intensity of radiation applied to a crystal interposed between the light input side of the multiplier tubes and the source of radiation. Because of imperfections and non-uniform geometric characteristics in the crystals as well as variations eminating from a source of radiation, the raw data may present aberrations in the clinical picture. These aberrations can be compensated for by deriving compensating mathematical factors on known data prior to taking the scan of a patient, utilizing data processing equipment.

Accordingly, it is an object of this invention to feed relatively large amounts of data within a short period of time via data busses directly into core memory of a central processing unit.

It is another object of this invention to circumvent the accumulator and allow faster data acquistion in the core memory than would otherwise be feasible.

It is a further object of this invention to provide the feeding of data through data channels to the computer memory in such a manner as to provide a "time share" basis to simultaneously acquire data from several head sources while also deriving calculations based on data from yet another source and displaying either data or derivations from yet another source.

It is a further object of this invention to provide apparatus for interfacing an analog-to-digital converter and a central processing unit in a system for scanning nuclear medical information where the interfacing is machine wired to provide a relatively uncomplicated construction of an otherwise complex matrix.

These and other objects of this invention can be more fully appreciated from further specification and claims below.

ON THE DRAWINGS

FIG. 38 is a diagrammatic view of angular relationship of central axes of apertures in a collimator used in a preferred embodiment of this invention;

FIG. 38a is a signal corresponding to functioning of apparatus illustrated in FIG. 38;

FIG. 38b is an electrical signal corresponding to functioning apparatus diagrammed in FIG. 39;

FIG. 38c is a representation of a signal generated by functioning of the apparatus diagrammed in FIG. 39;

Before explaining the present invention in detail, it is to be understood that the invention is not limited in its application to the details in construction and arrangement of parts illustrated in the accompanying drawings since the invention is capable of other embodiments and of being practiced or carried out in various ways. Also, it is to be understood that the phraseology and terminology employed herein are for the purpose of description and not of limitation.

AS SHOWN ON THE DRAWINGS

Figure 1:
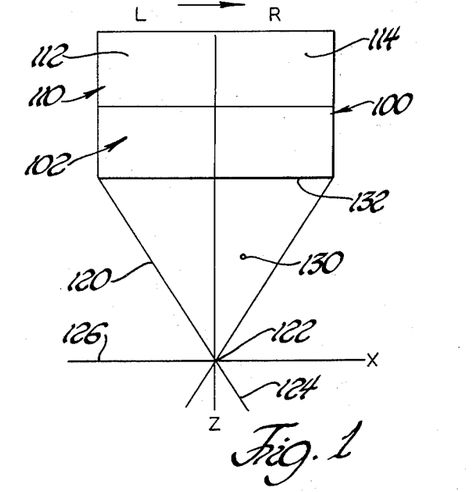
FIG. 1 is a transverse sectional view of a portion of the preferred embodiment of this invention.
Figure 28:
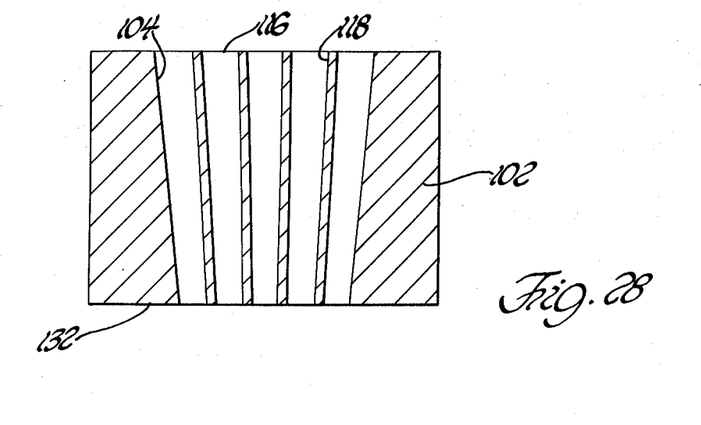
FIG. 28 is a transverse sectional view of the apparatus shown in FIG. 27.

FIG. 1 is a cross-sectional view of a portion of the apparatus used in the preferred embodiment of this invention. The head 100 comprises a collimator 102 similar to the one shown in FIG. 28. This collimator 102 comprises a plurality of angled channels 104 each having a central optical axis directed towards a common focusing point 122. Preferably, the size of each of these apertures 104 is such as to define, in cross-section, a hexagonal shape. This can be seen in the top of collimator 102, shown at 108.

Above the collimator 102 is a crystal structure 110. The crystal structure 110 is divided into a lefthand portion 112 and a righthand portion 114. Each of the crystal portions 112, 114 correspond to the left and right portions 116 and 118, respectively, of the collimator 102. Photomultiplier tubes, analog to digital apparatus, and general computer apparatus as well as oscilloscope apparatus are operatively connected to the structure shown in FIG. 1. These are not each separately illustrated Refering to FIG. 1, the area of radiation detection below the collimator is illustrated by the cone-shaped area, designated 120. This converges approximately at a point 122. It then diverges again into another conical shape 124 below a central plane of focusing 126. All of the apertures 104 in the collimator 102 are directed to point 122.

In FIG. 1, a source of radiation is indicated at numeral 130. It will be observed that this particular source of radiation is approximately midway between the common point of focusing 122 and the bottom 132 of the collimator 102.

Figure 11:
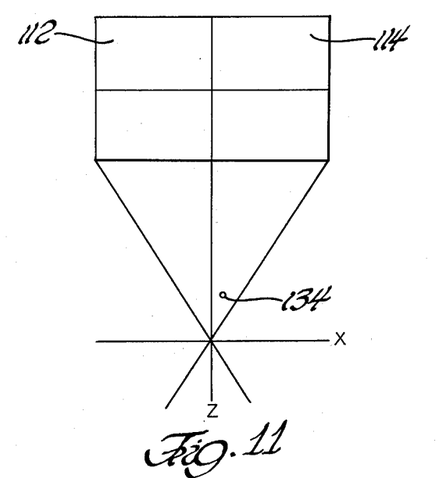
FIG. 11 is a cross-sectional view of the preferred embodiment of this invention.

FIG. 11 is a representative of identical apparatus shown in FIG. 1 except that the radiation of interest 134 is located substantially below the midpoint between the common point of focusing 122 and the bottom of the collimator 132. This radiation is proximate or very close to the point of focusing 122.

Figure 16:
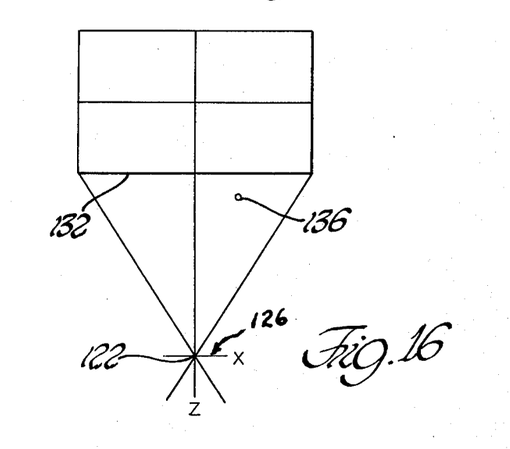
FIG. 16 is a cross-sectional view of a portion of the preferred embodiment of this invention.

FIG. 16 shows identical apparatus as that shown in FIGS. 1 and 11 with the exception that the point of radiation source 136 is located substantially above the midpoint between the common point of focusing 122 and the bottom of the collimator 132. This radiation is very close to the bottom of the collimator 132.

Figure 4:
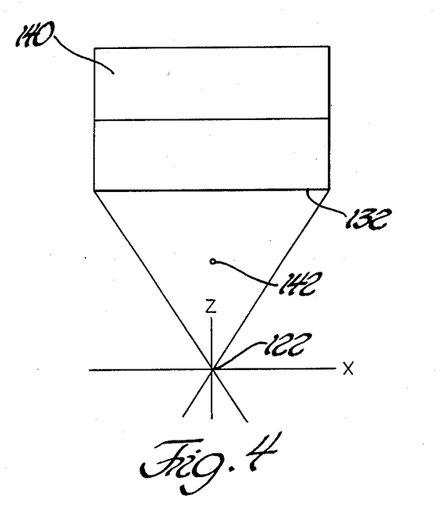
FIG. 4 is a transverse sectional view of a rectilinear scanner.

FIG. 4 is a cross-sectional view of a gamma ray imaging device similar to that shown in FIG. 1 except that instead of having separate crystal structures to detect separate sides of the collimator, a common crystal 140 is responsive to radiation from all of the apertures 104 within the collimator 102. The source of radiation indicated, at numeral 142, in FIG. 4, is at a position substantially indentical to the position of source of radiation 130 illustrated in FIG. 1.

Figure 14:
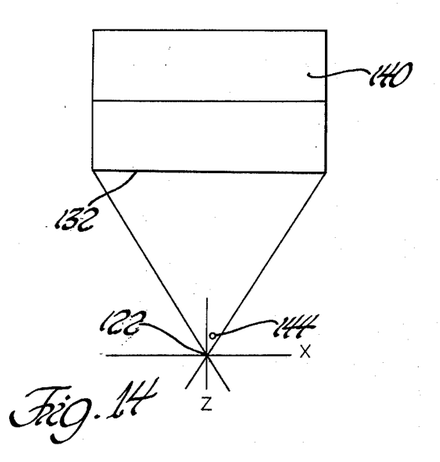
FIG. 14 is a cross-sectional view of a gamma ray rectilinear scanner.

FIG. 14 is illustrative of identical apparatus as that shown in FIG. 4 except that the source of radiation 144 is in a position substantially identical to the position of the source of radiation 134 illustrated in FIG. 11.

Figure 2:
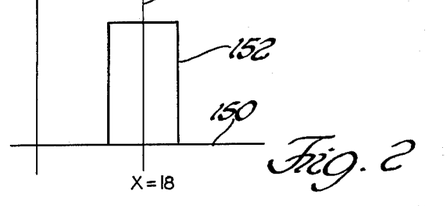
FIG. 2 is a graphical representation of a distinctly of a portion of the apparatus shown in FIG. 1.

FIG. 2 is a graphical representation of the response of crystal 114 shown in the apparatus illustrated in FIG. 1. The abscissa corresponds to channels (not used in the same sense as channels heretofore described) representative of lines in a 64 by 64 matrix used to represent the location of point count distributions over the area scanned by the head. More particularly, the abscissa 150 corresponds to the location of a source of radiation along the Y plane with respect to the X-Z plane shown in FIG. 1. The radiation response due to the source of radiation 130 in FIG. 1 is illustrated by pulse 152 having a central axis 154 that has a corresponding X value of 18 units.

Figure 3:
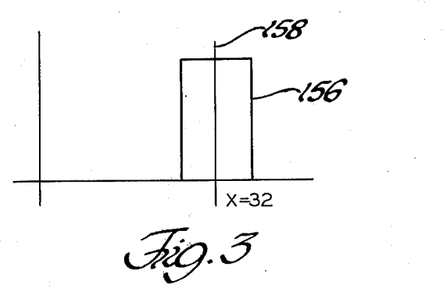
FIG. 3 is a graphical representation of a response from another portion of the apparatus shown in FIG. 1.

FIG. 3 is a graphical representation of the response of crystal 112 shown in FIG. 1 responding to source of radiation 130. The abscissa corresponds to a Y plane with reference to the X-Z planar representation shown in FIG. 1. A pulse 156 having a centroid 158 is illustrated in FIG. 3 corresponding to an X value equal to 32 units. It is understood that pulses represented in FIGS. 2 and 3 do not represent single pulses but rather a plurality of radiation detection events over a predetermined linear traverse.

Figure 5:
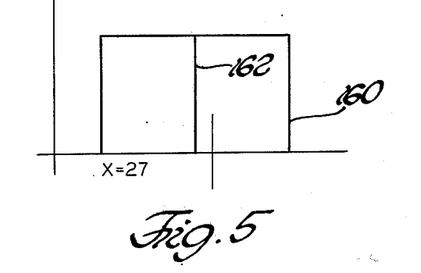
FIG. 5 is a graphical representation of a response of a portion of the apparatus shown in FIG. 4.

FIG. 5 is a graphical representation of the response of the apparatus, particularly crystal 140, as illustrated in FIG. 4, responding to source of radiation 142. This result is depicted on a graphical representation wherein the abscissa corresponds to a Y plane within the X-Z planar representation shown in FIG. 4. This response is shown as a pulse 160 having a centroid 162 corresponding to an X equal to 25 units. This pulse corresponds to a distribution of radiation detection events at a predetermined linear traverse. It is noted that pulse 160 has approximately twice the width of either of the pulses 152, 156 and that the centroid 162 of pulse 160 is midway between the centroids 154, 156.

It is noted with reference to FIGS. 2, 3, and 5 that the ordinate corresponds to the number of radiation events. Also, although the pulse representations are done in the form of square waves, more accurately, they should be Gaussian representations, that is having a bell-shaped curve. But, in order to more clearly understand the resolution capabilities of the invention, as hereinafter described, it is more illustrative of the invention to represent them as sharp distributions.

Figure 12:
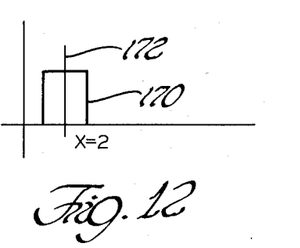
FIG. 12 is a graphical representation of a response of a portion of the apparatus shown in FIG. 11.
Figure 13:
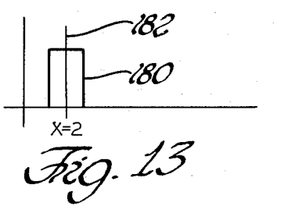
FIG. 13 is a graphical representation of the response of another portion of the apparatus shown in FIG. 11.
Figure 15:
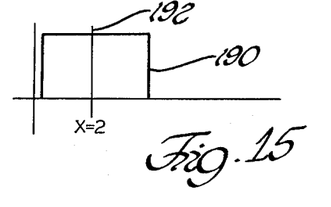
FIG. 15 is a graphical representation of the response of a portion of the apparatus shown in FIG. 14.

FIGS. 12, 13 and 15 are graphical representations of responses to sources 134, 134 and 144 respectively of crystal 112 in FIG. 11, crystal 114 in FIG. 11, and crystal 140 in FIG. 14, respectively, in a manner precisely analogous to the response depiction in FIGS. 2, 3 and 5 respectively.

Referring to FIG. 12, a pulse 170 having a centroid 172 corresponding to an X value equal to 2 is shown.

Referring to FIG. 13, a pulse 180 is shown having a centroid 182 corresponding to an X value equal to 4.

Referring to FIG. 15, a pulse 190 is shown having a centroid 192 corresponding to an X value equal to 3. It is noted that the pulse width 190 is approximately twice the width of pulses 170 and 180.

Figure 17:
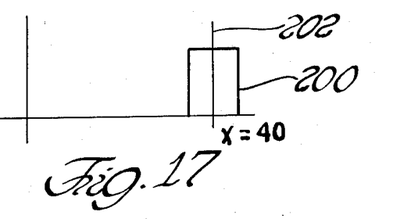
FIG. 17 is a graphical representation of the response of a portion of the apparatus shown in FIG. 16.
Figure 18:
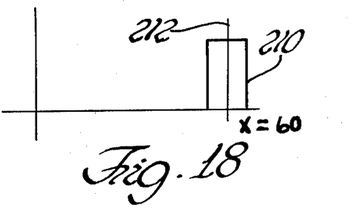
FIG. 18 is a graphical representation of the response of another portion of the apparatus shown in FIG. 16.

FIGS. 17 and 18 are graphical representations of the responses of crystals 114 and 112 respectively, of the apparatus illustrated in FIG. 16, in response to source of radiation 136. This depiction is in a manner analogous to the depiction of responses of crystals 114 and 112 in FIGS. 2 and 3 respectively, hereinbefore described.

Referring to FIG. 17, a pulse 200 is shown having a centroid 202 corresponding to an X value equal to 40.

Referring specifically to FIG. 18, a pulse 210 is shown having a centroid 212 corresponding to an X value equal to 60.

It is noted that the pulse height and width of pulses 200 and 210 are substantially identical. However, the position of their centroids 202 and 212 respectively indicate a difference that corresponds to the distance from the common focal point 122 in the sense of a displacement from a plane indicated at numeral 126.

The distance or displacement from one centroid to another with regard to right and left crystals 114 and 112 are determined by the prior traversal over the source of radiation of one crystal with respect to the other. Further, it is observed that the position of the centroid for a common traversal, referring to apparatus depicted in FIGS. 4 and 14, is approximately midway between the right and lefthand pulses if taken separately. The pulse width for the common is approximately double the width of the right or left taken separately. This phenomenon is observed due to the common exposure of the radiation taken as a whole in the common apparatus shown in FIGS. 4 and 14 as opposed to the discrete apparatus in FIGS. 1, 11 and 16.

It is also noted that the greater displacement of the centroids of the right and left pulses, the farther the point of radiation is removed from focusing point 122.

Figure 6:
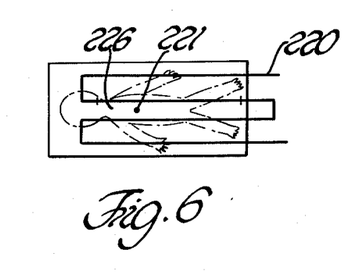
FIG. 6 is a top view of a patient showing the top of a rectilinear scan.

FIG. 6 is a top view of a patient on a table showing the path of a traversal or scan 220 taken by the apparatus shown in FIGS. 1, 4, 11, 14 and 16.

Figure 7:
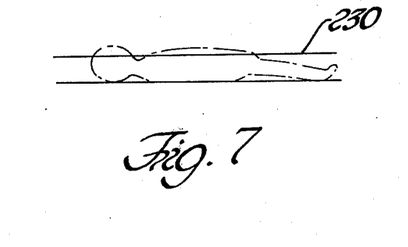
FIG. 7 is a partial transverse sectional view of the apparatus shown in FIG. 6 showing the plane of scanning.

FIG. 7 is a transverse sectional view of the apparatus shown in FIG. 6 showing the plane of focusing 230 in which the path 220 lies.

Figure 19:
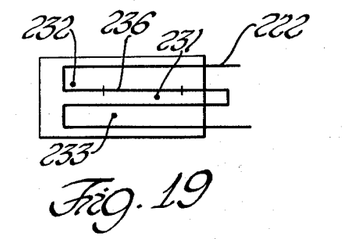
FIG. 19 is a top view of a portion of the preferred embodiment of this invention showing a rectilinear scan for predetermined locations of predetermined strengths of radiation.

FIG. 19 is a top view of a table showing the path of traversal 222 of a scanning device such as that shown in FIGS. 1, 4, 11, 14 and 16 wherein point sources 231, 232 and 233 are located in a predetermined manner with respect to distances to one another both horizontally and vertically and wherein the relative strength of radiation of these sources 231, 232 and 233 have been predetermined.

Figure 22:
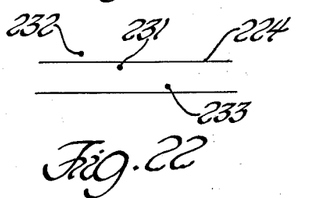
FIG. 22 is a top view of a portion of a rectilinear gamma ray imaging device.

FIG. 22 is a transverse sectional view of the apparatus shown in FIG. 19 showing the plane 224 in which the traversal path 222 is located with respect to the sources 231, 232 and 233.

Figure 8:
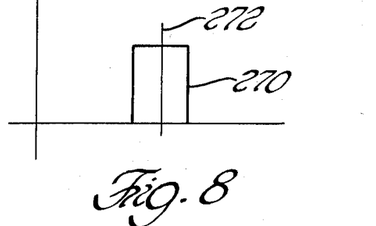
FIG. 8 is a graphical representation showing the response to several sources of radiation of a portion of the apparatus shown in FIG. 1.

FIG. 8 is a graphical representation of a radiation response of crystal 114 taken along portion of the path 220.

Figure 9:
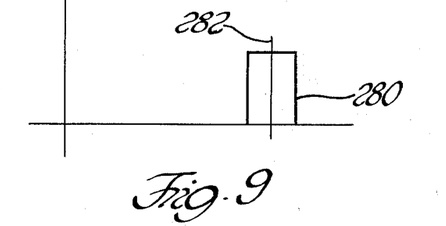
FIG. 9 is a graphical representation showng the response to several sources of radiation from another portion of the apparatus shown in FIG. 1.

FIG. 9 is a graphical representation of the response of crystal 112 taken along path 220.

Figure 10:
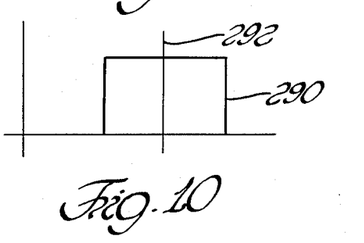
FIG. 10 is a graphical representation of the response from several sources of radiation from the apparatus shown in FIG. 4.

FIG. 10 is a graphical representation of the response of crystal 140 taken along the path of traversal 220.

Figure 20:
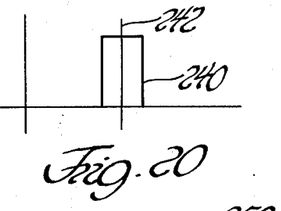
FIG. 20 is a graphical representation of the response of a portion of the apparatus shown in FIG. 19.

FIG. 20 is a graphical representation of the response of crystal 114 taken along the traversal of portion 236 of path 222.

Figure 21:
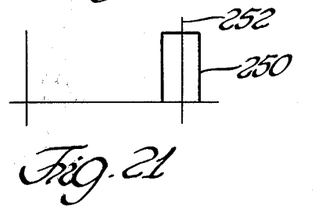
FIG. 21 is a graphical representation of the response of another portion of the apparatus shown in FIG. 19.

FIG. 21 is a graphical representation of the response of crystal 112 during the traversal of portion 236 of path 222.

Figure 23:
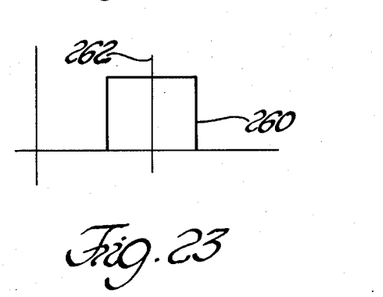
FIG. 23 is a graphical representation of the response of a portion of the apparatus shown in FIG. 22.

FIG. 23 is a graphical representation of crystal 140 during the traversal of portion 236 of path 222.

Figure 24:
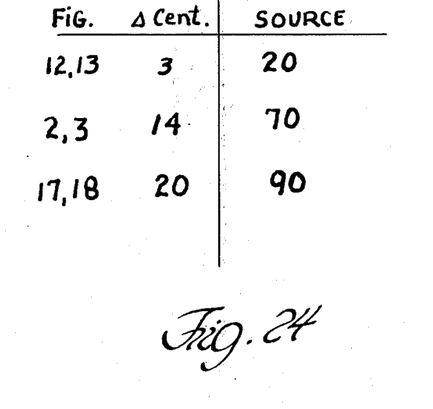
FIG. 24 is a chart comparing the separation of responses shown in FIGS. 2 and 3, 12 and 14, 17 and 18 with the displacement of radiation source from the focal plane.

FIG. 24 is a chart comparing the observed response depicted in FIGS. 2 and 3 with displacement from the focal plane.

This chart relates to the following:

| FIG. | Centroid Difference | Source Displacement |
|---|---|---|
| 12,13 | 3 | 20 |
| 2,3 | 14 | 70 |
| 17,18 | 20 | 90 |

The radiation displacement relates to percentage of displacement of head to common focal point at which the radiation source is located.

Figure 26:
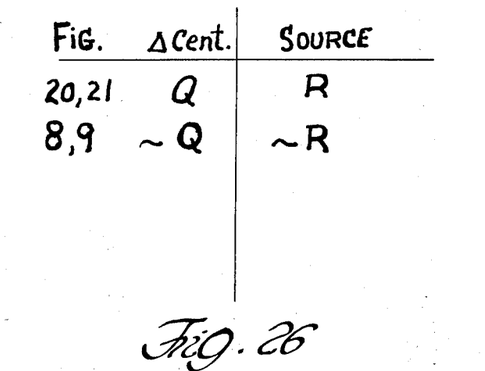
FIG. 26 is a chart comparing the separation of responses shown in FIGS. 20 and 21, and 8 and 9 with the calculated displacement of radiation source from the focal plane.
Figure 27:
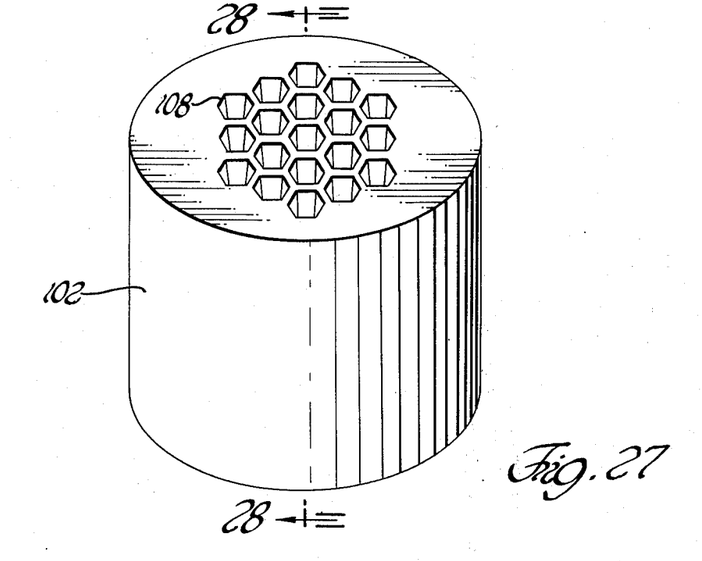
FIG. 27 is a three-dimensional projectional view of a portion of the preferred embodiment of this invention.

FIG. 26 is a chart comparing the responses depicted in FIGS. 20 and 21 with those calculated from FIG. 24.

This chart relates to the following:

| FIG. | Centroid Difference | Source Displacement |
|---|---|---|
| 20,21 | Q | R |
| 8,9 | approx. Q | approx. R |

Referring to FIG. 20, a pulse 240 is shown having a centroid at 242.

Referring to FIG. 21, a pulse 250 is shown having a centroid at 252.

Referring to FIG. 23, a pulse 260 is shown having a centroid at 262.

It is noted that the pulse width of pulse 260 is approximately double the width of either pulse 240 or 250. Further, the centroid 262 appears to be at a position along the abscissa midway between the positions on the abscissa of centroids 242 and 252.

Each of the FIGS. 20, 21 and 23 represent responses along the path 222 in FIG. 19 and response to source of radiation 231.

FIG. 8 indicates pulse 270 having a centroid at 272.

FIG. 9 illustrates a pulse 280 having a centroid at 282.

FIG. 10 illustrates a pulse 290 having a centroid at 292.

It is noted that the pulse width 290 is approximately double the pulse width 270 or 280. Further, it appears that the centroid 292 of pulse 290 appears at a position along the abscissa midway between the position of centroids 272 and 282.

It is noted further that while the pulse height of pulses 270, 280 and 290 do not bear a one-to-one correspondence to the pulse heights 240, 250 and 260. Nevertheless, the relative positions of the centroids 272, 282 and 292 do bear almost a one-to-one if not precisely a one-to-one correspondence to the position of centroids 242, 252 and 262, respectively.

Thus, FIGS. 8, 9 and 10 represent the responses of crystals 114, 112 and 140, respectively, to apparent source of radiation 221 indicated in the body of a patient shown in FIG. 6, where the relative position and strength of source 221 was *not predetermined*. In contrast, FIGS. 20, 21 and 23 represent the responses of crystals 114, 112 and 140 respectively to a *predetermined source of radiation* 231 along path 236 indicated in FIG. 19. Yet, it can be seen that there is a close correspondence of the centroids in FIGS. 8 and 20, and 9 and 21, and more precisely the difference between the locations of centroids 272 and 282 correspond to a similar distance between centroids 242 and 252. Therefore, an approximation of the depth, that is the displacement of source 221 from the focal point 222, can be observed to be similar to that known with a predetermined location of source 231. Thus, it can be concluded by simply observing the correspondence of these similar distances as illustrated in the charts indicated in FIGS. 24, and 26, that the separate but simultaneous scans of right and left portions of radiation passing through the collimator does give a depth approximation pursuant to this invention.

It can be further appreciated from the foregoing description that apparatus has been provided that not only allows for an approximation of depth by a table-look-up operation by computer, but, in addition, does allow for a more precise resolution independent of any depth calculation.

It can be still further appreciated from the foregoing description that a stereoscopic image of radiation corresponding to right and left eye views can be obtained by combining right and lefthand responses, such as that shown in FIGS. 2 and 3, in presenting simultaneous parallel right and lefthand images respectively of the same source of radiation. In an alternative embodiment of this invention, by simultaneously presenting views from right and lefthand sides of the collimator, a stereoscopic viewer such as that utililized in cameras or other optical devices, can be used by a human being to view the two images simultaneously in obtaining a depth perception.

Figure 31:
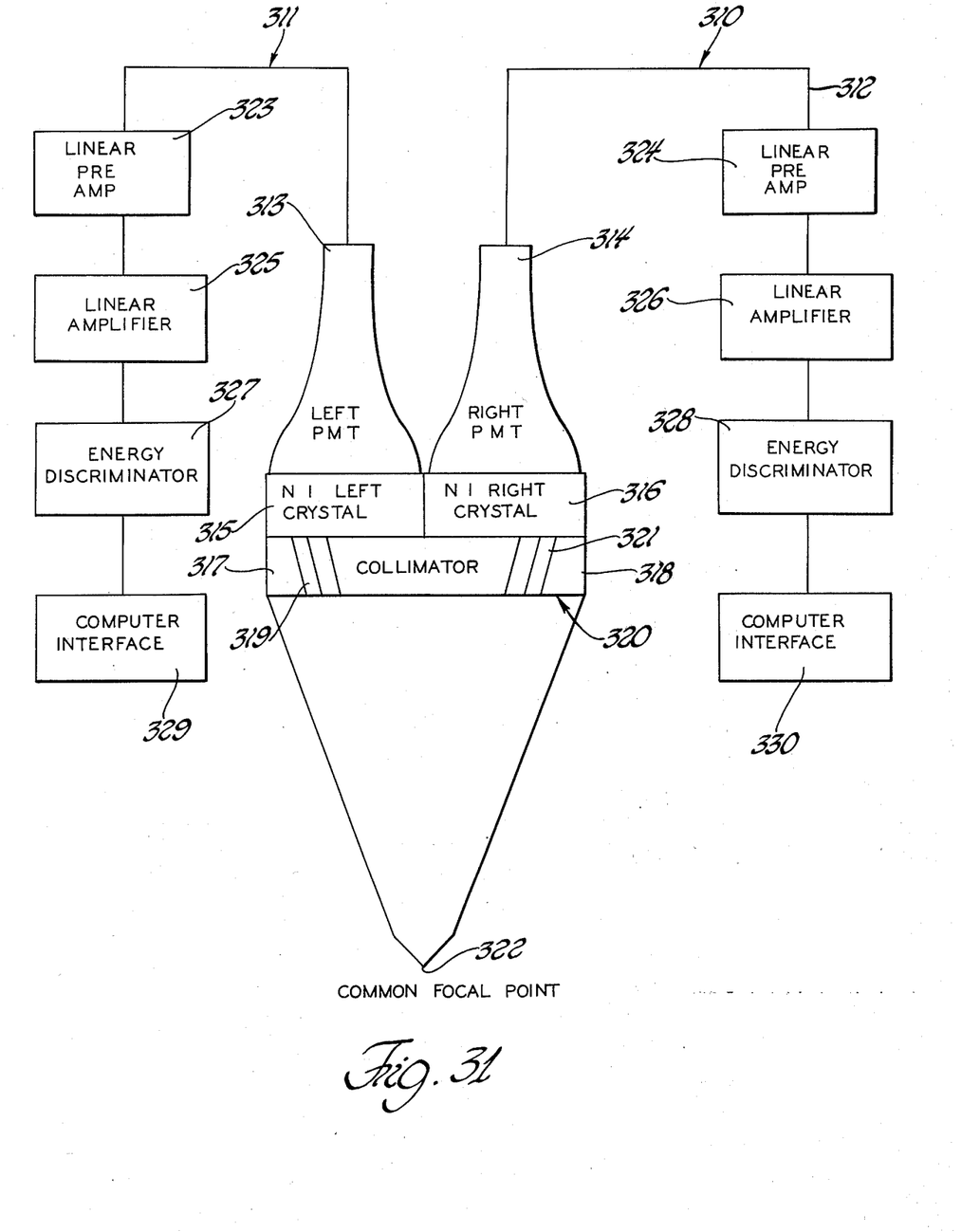
FIG. 31 is a partial schematic representation of electronic apparatus used to process information in the preferred embodiment of this invention.
Figure 31A:
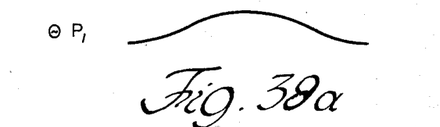
Figure 31B:
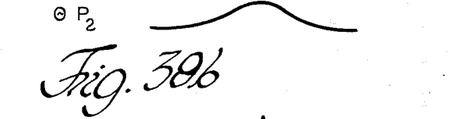
Figure 31C:
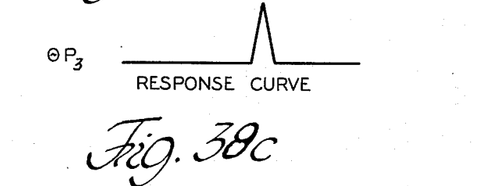

FIG. 31 is a diagrammatic representation showing in part a network associated with each of the two crystals in the preferred embodiment of this invention. The network is referred to generally at numeral 310. The network 310 comprises identical left and righthand portions 311 and 312 respectively. Each of these network portions receive information from a left and righthand photomultiplier tube (PMT) 313 and 314 respectively. Each of the photomultiplier tubes 313, 314 receive light signals from the crystal immediately below it, the left and righthand crystals 315 and 316 respectively. Each of the crystals receive impinging radiation from the left and righthand sides 317 and 318 respectively of a single collimator 320. The apertures 319, 321 are on the left and righthand sides respectively of the collimator 320 all focus at a common focal point 322.

The circuits 311 and 312 are identical, and each receive information separately from the left and righthand photomultiplier tubes 313 and 314 respectively. From the left photomultiplier tube, signals are fed to circuit 311. The first device in this circuit is a linear pre-amplifier 323. An example of the type of photomultiplier tube 313 utilized is photomultiplier tube designated RCA 6199 produced by the Radio Corporation of America. An example of a linear pre-amplifier 323 is Model 1405 scintillation pre-amplifier manufactured by Canbarra Industries of Middleton, Connecticut. Signals are fed from the linear pre-amplifier 323 to a linear amplifier 325 such as Canbarra double delay line amplifier designated DDL amplifier Model No. 1411. Signals from the linear amplifier 325 are fed to an energy discriminator 327 such as that made by Canbarra, designated Model No. 1431 single channel analyzer. Signals from the energy discriminator 327 are then fed to a computer interface channel 329.

Linear pre-amplifier 324, and linear amplifier 326, energy discriminator 328, and computer interface channel 330 are identical to corresponding linear pre-amplifier 323, linear amplifier 325, energy discriminator 327 and computer interface channel 329 respectively. The components linear pre-amplifier 324, linear amplifier 326, energy discriminator 328, and computer interface channel 330, process signals from the righthand photomultiplier tube only, as distinguished from corresponding components on the lefthand circuit which receive and process information only from the left photomultiplier tube 313.

Figures 34, 35, 36, 37:
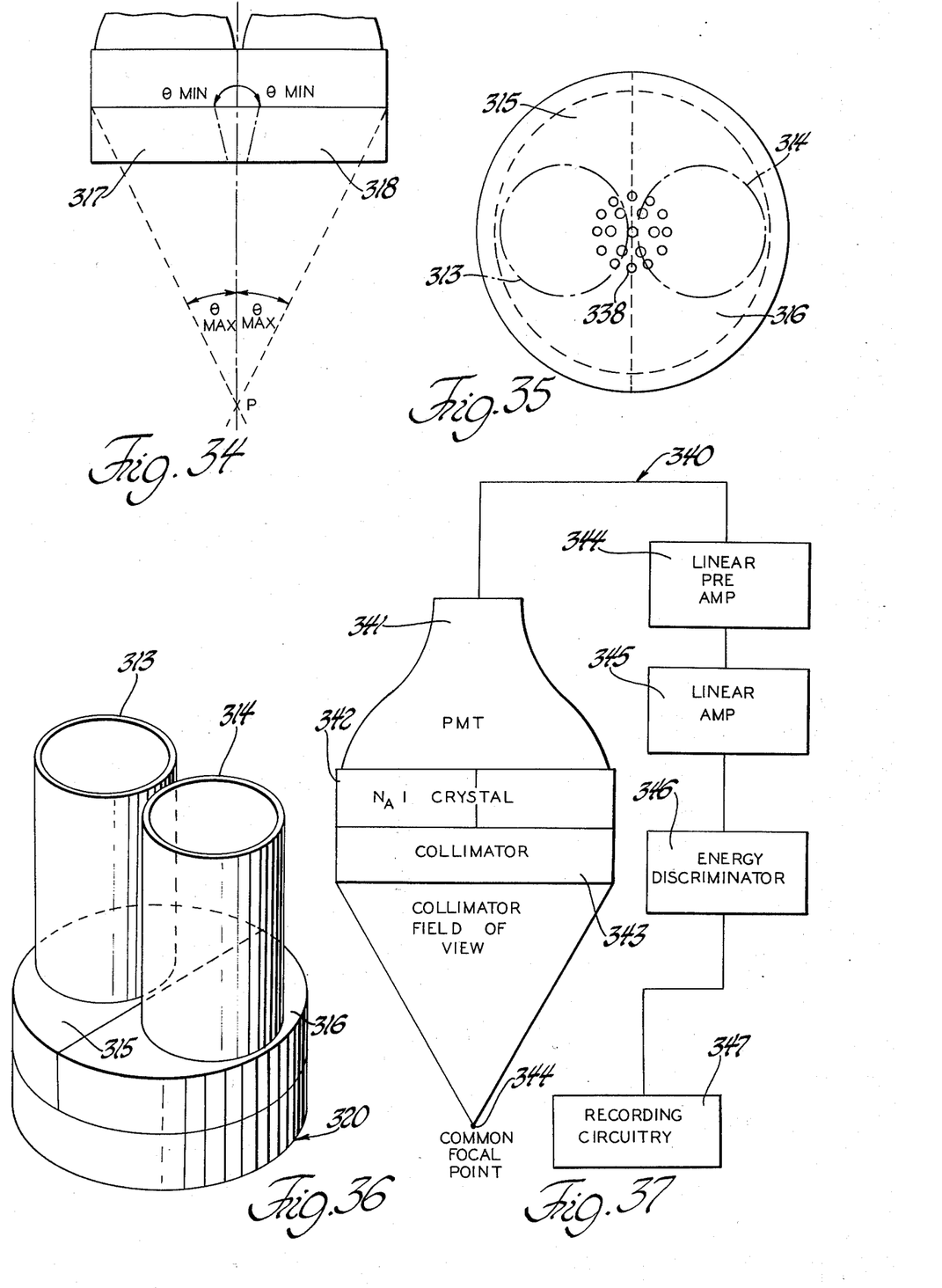
FIG. 34 is a diagrammatic view showing angular relationship of two crystals over a single collimator used in the preferred embodiment of this invention.
FIG. 35 is a partial top view of an embodiment of a portion of this invention.
FIG. 36 is a perspective view of a portion of the apparatus used in an embodiment of this invention.
FIG. 37 is a partial schematic view of electronic apparatus used with a single crystal collimator in contrast to the schematic representation shown in the preferred embodiment of this invention in FIG. 31.

The electronics illustrated in FIG. 31 compare with those illustrated in FIG. 37. In FIG. 37, a circuit 340 is designated generally. This is similar to the circuit 310 except that instead of having separate right and lefthand channels and corresponding components, there is a single channel and a single example of each component. Information is processed only from a single photomultiplier tube 341, which receives information from a single crystal 342, which is responsive to radiation passing through the collimator. The electronic components comprise the linear preamplifier 344, linear amplifier 345, and energy discriminator 346, and recording circuitry 347 and correspond in construction to linear pre-amplifier 323, linear amplifier 325, energy discriminator 327, and computer interface 329 respectively. It can be appreciated that the construction in FIG. 37 would not be capable of performing as the preferred embodiment of this invention illustrated in FIG. 31. This results because no depth calculation can be made or approximated due to the fact that radiation is not discriminated in terms of separate channels for aperture arrays being separately processed electronically to provide such comparison.

FIG. 36 illustrates an embodiment of this invention wherein photomultiplier tubes 313 and 314 are provided with separate semicircular disc crystals 315 and 316 respectively receiving information from a single collimator source 320.

FIG. 35 is a cross-sectional view of the collimator 320 showing the collimator apertures 338 and outline of the left and righthand crystals 315 and 316 respectively, and the outlines of the photomultiplier tubes at left and righthand sides 313 and 314, respectively.

FIG. 34 is a diagrammatic representation emphasizing the different angular and yet uniformly equal angular displacements of the centerlines of the apertures to a point P representing a common focal point from the left and righthand sides of the collimator, 317 and 318, respectively.

Figures 32, 32A, 32B, 32C, 33:
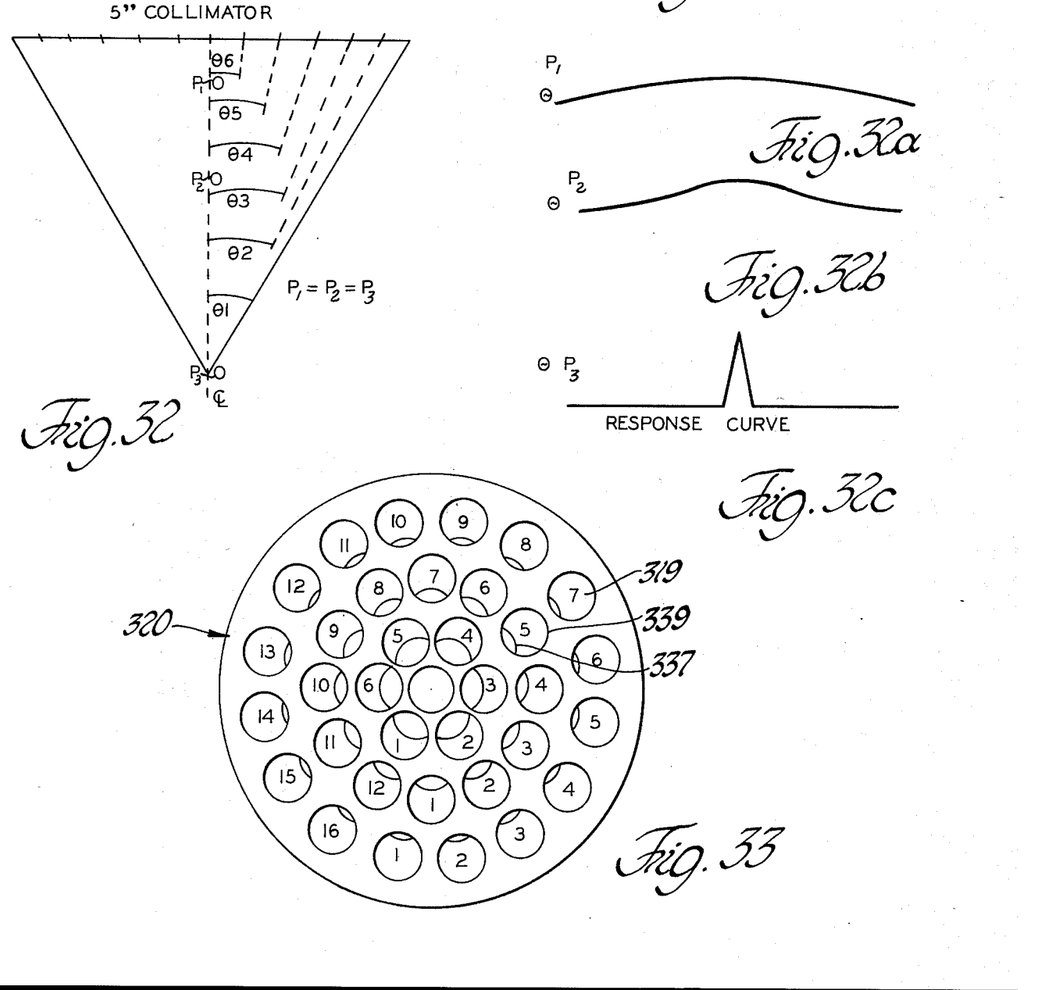
FIG. 32 is a diagrammatic representation showing angular displacement of central axes of collimator apertures.
FIG. 32a is a representation of a signal resulting from the functioning of the apparatus illustrated in FIG. 32.
FIG. 32b is a representation of a signal resulting from the functioning of the apparatus illustrated in FIG. 32.
FIG. 32c is a representation of a signal resulting from operation of apparatus illustrated in FIG. 32.
FIG. 33 is a top view of a collimator.

FIG. 33 is a top view of the collimator showing the angular displacement of the apertures 319 therein. It can be appreciated that the bottom border of the aperture 319, the bottom being designated 337, is angularly displaced from the top boundary of the same aperture 339.

FIGS. 32 and 38 represent the angular displacements of the centerline of apertures of different sized collimators and the different response curves therefrom. The difference in sharpness of the images $P_1$, $P_2$ and $P_3$ is illustrated in FIGS. 32a, 32b and 32c positions of sources $P_1$, $P_2$ and $P_3$ with respect to the common focal point as illustrated in FIG. 32. Likewise, a corresponding representation is made in FIGS. 38a, 38b and 38c with respect to FIG. 38. As illustrated in FIGS. 32 and 38, the centerlines of the apertures 319 focus on a common focal point. As can be observed in FIGS. 32a, 32b and 32c, the closer a source is to the common focal point of the apertures of the collimator, the sharper the image. This is also illustrated in FIGS. 38a, 38b and 38c.

Comparing FIGS. 32a with 38a, 32b with 38b, and 32c with 38c, the greater the displacement of the source of radiation from the common focal point of the apertures of a collimator, the more pronounced the sharpness of image of a smaller diameter collimator than that of a larger diameter collimator. In the preferred embodiment of this invention, by using separate discrete crystals for different arrays of apertures in a common collimator, the sharpness of image obtained with a common collimator is substantially retained even though a larger collimator is used.

"X" and "Y" signals are generated by electromechanical means for indicating the position of the traveling head during a scan, in a manner well known in the art. "Z" signals are generated by circuit means as discussed with respect to FIG. 36, above. These signals are fed to the analog-to-digital converter 440 illustrated in FIG. 25.

Figure 25:
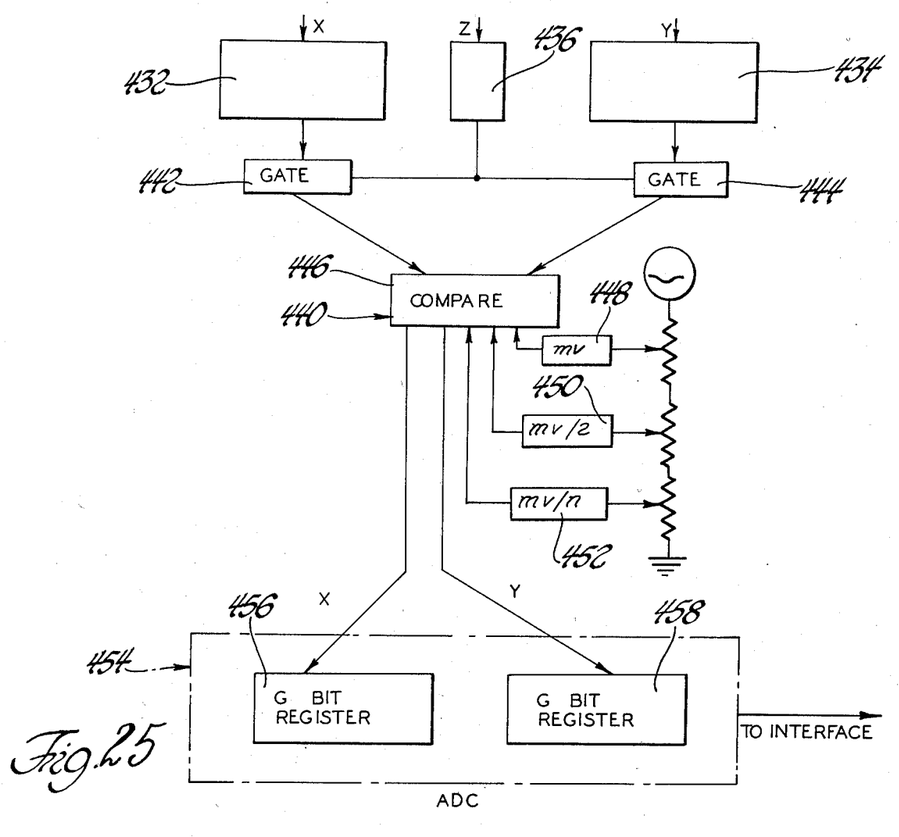
FIG. 25 is a flow chart representation of an analog to digital converter used in the preferred embodiment of this invention.

FIG. 25 is a flow chart representation of the aalog-to-digital converter (ADC) 440. The ADC comprises a pair of gates 442, 444 feeding a comparison circuit 446. Twelve comparison voltages (448, 450, 452 illustrated) for comparison purposes also feed the comparison circuit 446. A twelve bit register 454 is divided into six bit registers for X and Y components 456 and 458, respectively. These feed interface apparatus to be described hereinafter.

Each of the X and Y signals are fed to their respective gate circuits 442, 444. The Z signals activate the X and Y gates 442, 444 for feeding their respective signals to the comparison circuit 446. A source provides predetermined uniform pulses. These pulses are divided into twelve comparison signals. Each of the comparison signals have an amplitude that is one half raised to the $n$ power of the maximum comparison signal, where n varies from zero to five.

If the raw X or Y signals exceed a comparison signal, a corresponding digit is registered in the appropriate six bit register.

Figure 29:
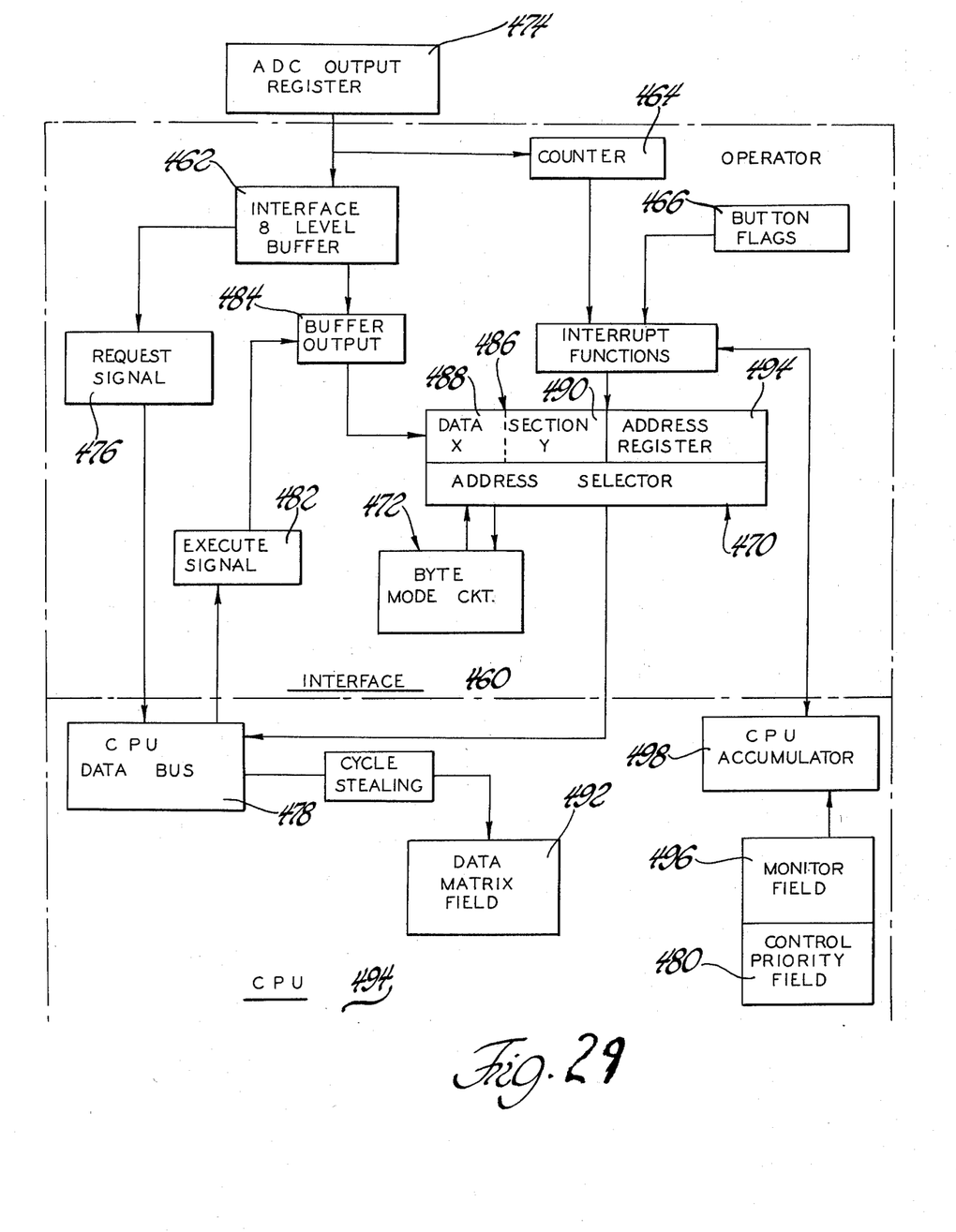
FIG. 29 is a flow chart representation of interface apparatus used in the preferred embodiment of this invention.

FIG. 29 is a flow chart representation of the interface apparatus 460. The interface apparatus comprises an eight level buffer 462, a counter 464, button flags 466, an address selector 470, and byte mode circuits 472. The entire interface apparatus is preferably made with integrated circuits and machine wired, in a manner well known in the art, rather than hand wired. The apparatus is purposely designed in matrix form, that although complex, can be machine wired to make construction relatively uncomplicated.

The ADC register 474 feeds a 12 bit signal into the interface eight level buffer 462. When a signal reaches the last level of the buffer, a request signal is generated by the interface buffer 476. This request signal is transferred to the central processing unit data bus 478. The data bus 478 transfers the signal to a control priority field 480. An executed signal 482 is generated back through the data bus to an apparatus 484 energizing buffer output. The buffer output is fed to the data section 486 of the address selector 470. The data section 486 has six bit registers 488, 490 corresponding to X and Y signals so that a number from 0 to 63 can be represented.

Each of these numbers corresponds to a position on a matrix memory location located in a data matrix field 492 of the core memory of the central processing unit 494. Appropriate address selection is determined by the address register portion 494 of the address selector 470. The central processing unit 494 has data processing functions that are capable of incrementing the data address by lowest bit. However in order to achieve certain matrix formats, it is desirable to increment the address register by the addition of byte signals. This is performed by the byte mode circuit 472. The byte mode circuit is activated by the monitor portion of a program located in the appropriate field 496 in core memory. This initiates a byte loop cycle in a manner well-known in the art.

The accumulator 498 can be interrupted from functioning by means of button flags. A counter 464 is activated by the ADC output. The counter 464 conditions the interrupt functions for operation. The effect that the interrupt function achieves is "cycle stealing" by stopping the accumulator and transfering the data directly from the address selector 470 of the interface 460 to the data bus 478. The data bus 478 then places the data directly in the data matrix field 480 of the core memory of the central processing unit 494. The operator can actuate the button flag 466.

Figure 30:
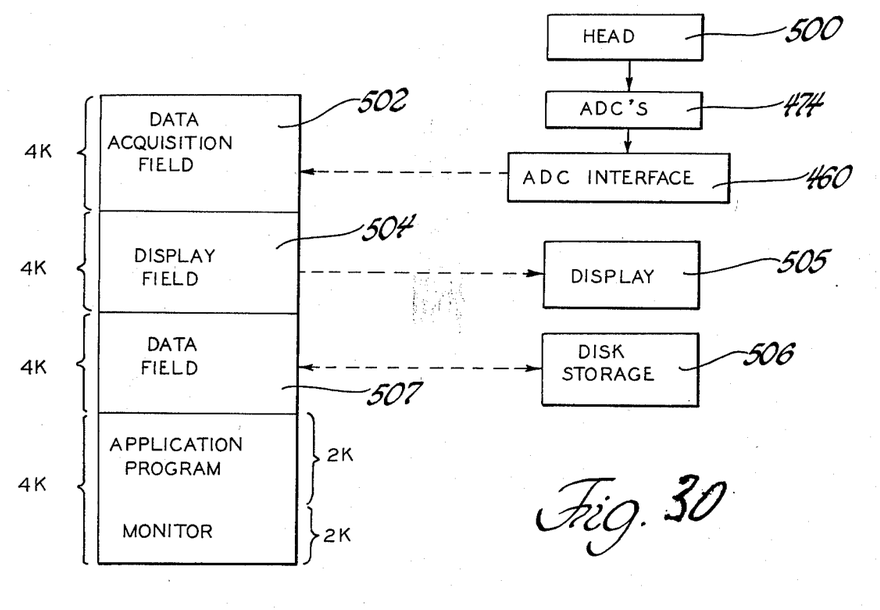
FIG. 30 is a flow chart representation showing various functions of the preferred embodiment of this invention.

FIG. 30 is a flow chart diagram showing the various functions of an embodiment of data processing apparatus used in an embodiment of the invention. It can be appreciated that while a few cycles of the computer are utilized during data acquisition in and transfering data initiated from the head, information can be processed by the aforementioned ADC, transfered to the interface 460, relayed to the data bus 478, and placed into the data acquisition field 502. After the end of the data acquisition series of cycles, an accumulator 498 can be activated for the display 505 of data from the display field 504, or to store the data in a data field 507 through a data bus to a disc storage 506, or to perform computations on a data field 507 and utilize the field for such computation and store the results on a disc.

The features of the above-described system relate to the utilization of a counter activated by the ADC output register and button flag activated by the operator. The accumulator is activated by a monitor field to provide an interrupt function for cycle stealing and allowing data acquisition on a "time share" mode while other functions such as derivation, display, and storage can be performed through the accumulator of the central processing unit after the cycle stealing phase has been completed.

The invention provides a method of image visualization whereby the operator is able to call upon digitized images stored upon a high speed magnetic storage device for presentation upon a cathode ray tube for diagnostic interpretation.

The invention allows the operator to display said digitized images while other functions are underway within the central processing unit. This is done without disrupting these other functions, and at the same time, preventing the central processing unit from missing data as a result of its enlarged usage.

In the preferred embodiment of this invention a dual 64 × 64 resolution is utilized (for both stereo pairs) as if it were the one and only matrix configuration. Actually three configurations are available: 32 × 32; 64 × 64; and 128 × 128. For purposes of illustration it is fruitful to think of a 64 square matrix while being aware of other immediately above-mentioned variations.

In referring to FIG. 29 it should be noted that the address selector has three components first subdivided into an address register and data section. The address register is also interpreted as a data field register. The data section is divided into Y and X components. The data field registration Y and X components feed into the address selector.

In different modes of operation the size of each field varies as follows:

Mode: 64 squared-word
   Data field registration: 3 bits;
   Y: 6 bits;
   X: 6 bits;
   Total address bits: 15 bits;
Mode 64 squared-byte
   Data field registration: 4 bits;
   Y: 6 bits;
   X: 5 bits;
   Total address bits: 15 bits;
Mode 32 squared-byte
   Data field registration: 6 bits;
   Y: 5 bits;
   X: 4 bits;
   Total address bits: 15 bits;
Mode 128 squared-byte
   Data field registration: 2 bits;
   Y: 7 bits;
   X: 6 bits;
   Total address bits: 15 bits.

Referring to FIG. 25, the register can be divided into five or more bit registers for X and Y components in embodiments of this invention. A source of predetermined pulses are divided such that each of the comparison signals are exactly twice as large as the next feeding signal, thereby forming a binary sequence of up to twelve bits, in the six bit register format.

In a preferred embodiment of this invention, the scanner conforms to the above discussion relating to FIGS. 1–28; and the signals from that scanner are processed by apparatus discussed above relative to FIGS. 25, 29, 30, utilizing electronic apparatus referred to in the above discussion relative to FIGS. 31–38.

We claim:

1. In a tomographic gamma ray imaging device for detecting radiation dispersed within or transmitted through a patient and displaying an illustration of such distribution, the improvements comprising:
   a head traversing the patient;
   said head having a collimator;
   a plurality of crystal members mounted on top of said collimator within said head;
   said collimator comprising a lead shield relatively impervious to the passage of gamma radiation;
   arrays of apertures within said collimator allowing the conduction of gamma radiation through said apertures;
   each of said apertures having a focal axis directed towards a point below said collimator;
   said point lying on the focal axes of all of said apertures;
   said point lying within a focal plane from which radiation is detected by said head through said apertures in said collimator;
   each of said crystal members responding electromagnetically to radiation from a different one of the arrays of apertures in said collimator;
   each of said crystal members responding to radiation simultaneously to each of the other crystal members responding to radiation;
   each of said focal axes of said apertures intercepting with one another and being at acute angles with respect to each other;
   said head passing over a source of radiation in such a manner that electromagnetic response from one of said crystal members is discrete from and chronologically displaced from an electromagnetic response of another one of said crystal members.

2. In the apparatus of claim 1, photomultiplier tube members each responding to electromagnetic signals generated by one of said crystal members;
   means communicating the response of said photomultiplier tube members to an oscillograhic display member;
   said oscillographic display member operable to receive response from said photomultiplier tube members in separate and distinct channels which, in turn, each separately and distinctly respond to electromagnetic signals from one of said crystal members;

said oscillographic display member operable to simultaneously separately and distinctly display the responses received along said separate channels.

3. In the apparatus of claim 2, an optical viewer having two lenses with parallel optical axes focused on parallel but separate and distinct images displayed on said oscillographic display member where each such image is responsive to a different one of said separate channels.

4. In the apparatus of claim 2, the further improvements comprising:

an array of photomultiplier tube members each responding to electromagnetic signals generated by one of said crystal members;

an array of linear preamplifiers each generating an electrical signal responsive to said response from different one of said photomultiplier tube members;

an array of linear amplifiers each generating a signal responsive to said electrical signal from a different one of said linear preamplifiers;

an array of energy discriminators each emitting signals within predetermined amplitude limits responsive to said signals being generated from a different one of said linear amplifiers;

a computer interface apparatus emitting signals within a form cognizable by a central processing unit of a digital computer, each such signal being responsive to said signals being emitted by a different one of said energy discriminators;

and means operable to calculate and display mathematical and graphical representations of said distribution responsive to said computer interface emitting signals.

5. In the apparatus of claim 1, the further improvements comprising:

a plurality of photomultiplier tube members;

each of said photomultiplier tube members being responsive to electromagnetic radiation from one of said crystal members;

each of said photomultiplier tube members being unresponsive to another one of said crystal members;

each one of said photomultiplier tube members responsive to electromagnetic signals from a different one of said crystal members simultaneously to another one of said photomultiplier tube members being responsive to another one of said crystal members;

an analog to digital converter having a plurality of channels;

each of said channels being responsive to one of said photomultiplier tube members but being unresponsive to any of the other of said photomultiplier tube members;

a general purpose computer apparatus having a plurality of arrays of data channels;

one array of said data channels being responsive to one of said channels in said analog to digital converter;

said one array of data channels being unresponsive to other channels in said analog to digital converter;

data manipulation means in said computer being operable to massage data entered into the general computer apparatus through said data channels;

means for separately and discretely storing information after said data massage from a different one of each of said arrays of data channels;

and means for displaying the results of said data massage.

6. In the apparatus of claim 5, the improvements comprising:

said display means comprising oscillographic means for simultaneous two-dimensional representation of data massage results eminating from a different one of said arrays of data channels;

said oscillographic means also having electrical means for displaying mathematical, graphical representations of massaging data from a different one of each of said arrays of data channels;

and means for collating responses from different arrays of data channels into a single representation illustrative of depth calculations.

7. In the apparatus of claim 1, the further improvments comprising:

an array of photomultiplier tube members each responding to electromagnetic signals generated by one of said crystal members;

an array of linear preamplifiers each generating an electrical signal responsive to said response from different one of said photomultiplier tube members;

an array of linear amplifiers each generating a signal responsive to said electrical signal from a different one of said linear preamplifiers;

an array of energy discriminators each emitting signals within predetermined amplitude limits responsive to said signals being generated from a different one of said linear amplifiers;

a computer interface apparatus emitting signals within a form cognizable by a central processing unit of a digital computer each such signal being responsive to said signals being emitted by a different one of said energy discriminators.

8. In the apparatus of claim 7, the further improvements comprising:

said computer interface apparatus comprising an interface leveling buffer, a buffer output, an address selector, an interrupt function apparatus, a counter and a byte mode circuit;

said central processing computer comprising a data bus member, an accumulator and a memory storing device;

said interface leveling buffer operable to send a request signal to said data bus member responsive to said signals and emitting from said energy discrimnator;

said data bus member operable to transmit an execute signal to said buffer output responsive to said request signal received from said address selector;

said interrupt function apparatus operable to enable said address selector for operation responsive to a signal received from said counter;

said central processing unit data bus member operable to transmit data to a data field within said memory device without passing such data through said accumulator;

said accumulator operable to derive information from said data field responsive to instructions from a stored program within said memory device;

whereby data reflective of radiation passing through said collimator can be stored in the data field of said memory device while being interleaved with other simultaneous operations of said central processing unit being processed through the accumulator of said central processing unit.

9. In the apparatus of claim 8, the further improvements comprising:
a derived calculation field within said memory storage device;
said central processing unit deriving calculations from data stored in said data field responsive to a stored program stored within said memory device;
said other simultaneous operations comprising the derivation of calculations by said central processing unit and storage of the results in said derived calculation field.

10. In the apparatus of claim 8, the further improvements comprising:
a display field within said memory storage device;
said central processing unit operable to calculate display information from data stored in said data field and store the resultant display information in said display field responsive to a stored program within said memory device;
an oscillographic display member operatively connected to said central processing unit and operable to display said display information from said display field responsive to a stored program within said memory storage device;
said other simultaneous operations comprising the calculation and storage of said display information by said central processing unit and display of said display information by said display member.

11. In the apparatus of claim 10, the further improvements comprising:
said display field being subdivided into sub-fields where each said sub-field corresponds to display information for one corresponding sub-field of said data field where the data in that sub-field is derived from the signals of one of said energy discriminators;
said oscillographic display member being operable to separately, distinctyl, and simultaneously display the display information from each of said sub-fields in said display field;
a derived calculation field within said memory storage device;
said central processing unit deriving calculations from data stored in said data field responsive to a stored program stored within said memory device;
said derived calculation field being subdivided into sub-fields where each said sub-field corresponds to derived calculations for one corresponding sub-field of said data field where the data in that sub-field is derived from the signals of one of said energy discriminators;
said other simultaneous operations further comprising the derivation of calculations by said central processing unit and storage of the results in said derived calculation field.

12. In a method of tomographic gamma ray imaging, the improvements comprising:
scanning gamma radiation along a predetermined planar path;
shielding a preselected portion of radiation from detection;
shielding another portion of radiation from detection simultaneously;
simultaneously funneling radiation through a preselected portion of said shielding;
simultaneously funneling another portion of radiation through another portion of shielding;
said funneling having a common point of intersection on a central focal plane;
discretely, separately, and simultaneously obtaining crystalographic electromagnetic response from said separate preselected funneling of radiation;
counting by photomultiplication in separate channels in a discrete and simultaneous manner the separately detected electromagnetic radiation;
converting resultant electromagnetic signals in continuous form to discrete pulsating digital signals in separate channels simultaneously from said counting by photomultiplication;
channeling the digitized data into computer data banks and maintaining the separate and distinct separation thereof provided by previous steps;
massaging the data by data processing in said computer;
and simultaneously illustrating resultant tomographic radioactive counts on a predetermined matrix separately and distinctly for the previously channeled and separated flow of signals.

13. In a tomographic gamma ray imaging device for detecting radiation dispersed within a patient and displaying an illustration of such distribution in a mathematical and graphical representation of such distribution, the improvements comprising:
a head;
said head having a colllimator;
a crystal member mounted on top of said collimator within said head;
said collimator comprising a lead shield relatively impervious to the passage of gamma ray radiation;
an array of apertures in said collimator allowing the conduction of gamma ray radiation through said apertures;
each of said apertures having a focal axis directed towards a point below said collimator;
said point lying on the focal axis of each of said apertures;
said point lying within focal plane from which radiation is detected by said head through said apertures in said collimator;
each said focal axis of said apertures intercepting with one another and being at an acute angle with respect to each other;
said crystal emitting a light signal responsive to nuclear radiation passing through said array of apertures;
a photomultiplier tube emitting a signal responsive to light emitted from said crystal;
a linear preamplifier generating an electrical signal responsive to said signal from said photomultiplier tube;
a linear amplifier generating a signal responsive to said signal being generated from said linear preamplifier;
an energy discriminator emitting signals within predetermined amplitude limits responsive to said signal being generated from said linear amplifier;
a machine wired computer interface apparatus emitting a signal within a form cognizable by a central processing unit of a digital computer responsive to said signals being emitted by said energy discriminator;

said computer interface apparatus comprising an interface leveling buffer, a buffer output, an address selector, an interrupt function apparatus, a counter, and a byte mode circuit;

said central processing computer comprising a data bus, an accumulator and a memory storing device;

said interface leveling buffer operable to send a request signal to said data bus responsive to said signals emitting from said energy discriminator;

said data bus operable to transmit an execute signal to said buffer output responsive to said request signal received from said address selector;

said interrupt function apparatus operable to enable said address selector for operation responsive to a signal received from said counter;

said central processing unit data bus operable to transmit data to a data field within said memory device without passing such data through said accumulator;

said accumulator operable to derive information from said data field responsive to instructions from a stored program within said memory device;

whereby data reflective of radiation passing through said collimator can be stored in the data field of said memory device while being interleaved with other simultaneous operations of said central processing unit being processed through the accumulator of said central processing unit.

* * * * *